US011965829B2

(12) United States Patent
Voisin et al.

(10) Patent No.: US 11,965,829 B2
(45) Date of Patent: Apr. 23, 2024

(54) DEVICE FOR ANALYSING GRAINS BY MEANS OF INFRARED AND FLUORESCENCE SPECTROSCOPY

(71) Applicant: Spectralys Innovation, Romainville (FR)

(72) Inventors: Clément Voisin, Paris (FR); Olivier Charles-Francois, Paris (FR); Papus Boutaouakou, Chessy (FR); Monji Messaoudi, Aubervilliers (FR); Stéphane Oddos, Boulogne Billancourt (FR)

(73) Assignee: Spectralys Innovation, Romainville (FR)

( * ) Notice: Subject to any disclaimer, the term of this patent is extended or adjusted under 35 U.S.C. 154(b) by 639 days.

(21) Appl. No.: 17/258,961

(22) PCT Filed: Jul. 12, 2019

(86) PCT No.: PCT/EP2019/068916
§ 371 (c)(1),
(2) Date: Jan. 8, 2021

(87) PCT Pub. No.: WO2020/012029
PCT Pub. Date: Jan. 16, 2020

(65) Prior Publication Data
US 2021/0123861 A1 Apr. 29, 2021

(30) Foreign Application Priority Data

Jul. 13, 2018 (FR) ...................................... 1856531

(51) Int. Cl.
*G01N 21/3563* (2014.01)
*G01N 21/3554* (2014.01)
(Continued)

(52) U.S. Cl.
CPC ...... *G01N 21/3563* (2013.01); *G01N 21/3554* (2013.01); *G01N 21/6486* (2013.01); *G01N 33/10* (2013.01); *G01N 2021/8592* (2013.01)

(58) Field of Classification Search
CPC .... G01N 21/35; G01N 21/64; G01N 21/3581; G01N 21/359
See application file for complete search history.

(56) References Cited

U.S. PATENT DOCUMENTS 8,184,274 B2   5/2012  Bruins
2009/0255473 A1*  10/2009  Katz .................. A23C 19/02
                                                                 119/14.08
(Continued)

FOREIGN PATENT DOCUMENTS

DE       10119763 A1    10/2002
EP        1850117 A1    10/2007
(Continued)

OTHER PUBLICATIONS

Bertrand, Dominique, et al., "La spectroscopie infrarouge et ses applications analytiques" ("Infrared spectroscopy and the analytical applications thereof"), 2006, [book abstract only, online], retrieved Jan. 7, 2021, retrieved from the Internet <URL: https://translate.google.com/translate?hl=en&sl=fr&u=https://www.industrie-techno.com/article/la-spectroscopie-infrarouge-et-ses-applications-analytiques.4986&prev=search&pto=aue> (12 pages).
(Continued)

Primary Examiner — Hina F Ayub
(74) Attorney, Agent, or Firm — Alston & Bird LLP

(57) ABSTRACT

A device for spectroscopically analysing a grain sample may include a first infrared analysis module, a second fluorescence analysis module, a third specific weight analysis module and a processing module. Each of the first and second modules may include a measurement chamber, an excitation submodule to emit at least one electromagnetic
(Continued)

radiation towards at least a portion of the sample, a measurement submodule, and a draining system. The third analysis module may include a container, and a measurement submodule to measure a specific weight of the sample. A processing module may be connected to each of the modules and may include a memory to receive data transmitted by a communication network, the data including electromagnetic spectra acquired and specific weights measured, and a processor to couple the data received in the memory and to determine an indicator of quality of the sample from the coupled data.

7 Claims, 7 Drawing Sheets

(51) Int. Cl.
  *G01N 21/64* (2006.01)
  *G01N 21/85* (2006.01)
  *G01N 33/10* (2006.01)

(56) References Cited

U.S. PATENT DOCUMENTS

2010/0014070 A1* 1/2010 Bruins ............... G01N 21/85
  356/72
2019/0369013 A1 12/2019 Birlouez-Acharid et al.

FOREIGN PATENT DOCUMENTS

EP         2148185 A2       1/2010
WO    WO 2017/134050 A1    8/2017

OTHER PUBLICATIONS

Borràs, Eva, et al., "Data fusion methodologies for food and beverage authentication and quality assessment—A review", *Analytica Chimica Acta*, Sep. 3, 2015, pp. 1-14, vol. 891, Elsevier B.V.

Sádecká, Jana, et al., "Fluorescence Spectroscopy and Chemometrics in the Food Classification—A Review", *Czech Journal of Food Sciences*, 2007, pp. 159-173 vol. 25, issue 4, Czech Republic.

National Industrial Property Institute, Preliminary Search Report and Written Opinion for French Application No. FR 1856531, dated Jan. 10, 2019, 9 pages, Republic of France.

International Searching Authority (ISA), International Search Report and Written Opinion for International Application No. PCT/EP2019/068916, dated Oct. 7, 2019, 16 pages, European Patent Office, Netherlands.

* cited by examiner

DEVICE FOR ANALYSING GRAINS BY MEANS OF INFRARED AND FLUORESCENCE SPECTROSCOPY

CROSS-REFERENCE TO RELATED APPLICATIONS

This application is a national stage application filed under 35 U.S.C. § 371 of International Application No. PCT/EP2019/068916 filed Jul. 12, 2019, which application claims priority to French Application No. 1856531 filed Jul. 13, 2018, each of which is hereby incorporated by reference in its entirety.

The invention relates to the field of spectroscopic analysis. In particular, the invention relates to a device for measuring properties of a sample by fluorescence spectroscopy and by infrared spectroscopy.

BACKGROUND OF THE INVENTION

The invention can be applied in particular, but not solely, to the pharmaceutical industry, to the environmental industry or also the food industry. In the food industry, industrial procedures require a precise knowledge of the technological, nutritional and/or toxicological properties of the samples analysed. In this framework, the analysis of samples by means of spectroscopic techniques makes it possible to extract parameters from them with a high physico-chemical informational content.

To measure these parameters precisely and in compliance with industrial standards, it is known spectroscopy devices which resort to different methods. In particular, in the case of grain samples, fluorescence spectroscopy and infrared spectroscopy make it possible to separately measure different parameters of these samples.

However, a disadvantage of known devices is that they are only designed to function in small spaces, for example in silo or factory laboratories, with a highly reduced analysis time, i.e. about 1 to 3 minutes per sample. Yet, the measurement must be taken twice: on the one hand, by means of a fluorescence spectroscopic device and on the other hand, by means of an infrared spectroscopic device. Such separate devices therefore involve an increased time, an increased space and an increased acquisition cost, a management of more complex data, as each instrument is controlled by different processing means and software, and monitoring logistics of the devices and more difficult measurement sites. Furthermore, the reliability and consistency of measurements taken by means of separate devices is significantly reduced, since these measurements are taken on different samples.

Moreover, another disadvantage is that the known devices significantly complicate the joint processing of measurements obtained from several different spectroscopic technologies. Thus, known devices are often limited to determining the parameters of a sample separately and are not adapted to measure them in a combined manner, for example via a joint processing of fluorescence spectroscopy measurements in ultraviolet fields and infrared spectroscopy measurements.

In known devices, the measurement and the processing of data coming from these two types of spectroscopy are carried out within separate devices and not coupled, which highly limits their joint use, and thus the resulting synergies in the data analysis. The lack of technical convergence between the two acquisition modes also makes the task more difficult and more complex.

OBJECT AND SUMMARY OF THE INVENTION

The invention aims to overcome at least one of the abovementioned disadvantages.

To this end, the present invention proposes one single device capable of taking a measurement of fluorescence spectra, infrared spectra and specific weight on one same sample.

An aspect of the invention thus relates to a device for spectroscopically analysing a grain sample, characterised in that said device comprises a first infrared analysis module, a second fluorescence analysis module, a third specific weight analysis module and a processing module, each of said first module and second module comprising
  a measurement chamber configured to receive at least a portion of the sample;
  an excitation submodule configured to emit at least one electromagnetic radiation towards said at least a portion of the sample;
  a measurement submodule configured to acquire at least one electromagnetic spectrum of the sample;
  a draining system configured to guide the sample towards said third module;
  the third analysis module comprising
  a container configured to receive the sample;
  a measurement submodule configured to measure a specific weight of the sample;
  said processing module being connected to each of the analysis modules by a communication network and comprising
  a memory configured to receive data transmitted by said communication network, said data comprising electromagnetic spectra acquired and specific weights measured; and
  a processor configured to organise and couple data received in the memory and to determine a quality indicator of the sample from the coupled data.

According to different additional characteristics of said device, which could be taken together or separately:
  the excitation submodule of the first infrared analysis module is configured to emit at least one electromagnetic radiation of wavelength comprised between 600 and 2500 nanometres, and wherein the measurement submodule of the first infrared analysis module comprises a spectrometer configured to acquire at least one absorbance and/or transmittance spectrum;
  the excitation submodule of the second fluorescence analysis module is configured to emit at least one electromagnetic radiation of wavelength comprised between 200 and 800 nanometres and the submodule of the second fluorescence analysis module comprises a spectrometer configured to acquire at least one spectrum selected from among: a fluorescence spectrum in frontal mode, acquired at an angle comprised between 30 and 60° with respect to the surface of the sample, i.e. a conventional fluorescence spectrum, acquired at a right angle, a wavelength of said at least one spectrum being comprised between 200 nanometres and 800 nanometres;
  said device further comprises a funnel configured to guide at least a portion of the sample towards the first module and the second module;

said quality indicator of the sample is chosen from among: a Hagberg falling number, a mycotoxin contamination rate, an acrylamide contamination rate, a humidity rate, a protein rate, a sugar content, a hardness, a baking strength or other characteristic typical of flours, a particle size or also a specific weight;

the height of the device is less than 75 centimetres, preferably less than 60 centimetres, the width of the device is less than 70 centimetres, preferably less than 55 centimetres, and the depth of the device is less than 55 centimetres, preferably less than 50 centimetres.

Advantageously, the device makes it possible for a successive and/or simultaneous measurement of spectral data and of specific weight data of a sample, which brings an informational synergy improving the performance of the quality indicator prediction, usually measured by only one of the infrared or fluorescence technologies.

Advantageously, the presence of a measurement submodule configured to measure a specific weight of a sample provides a weighing means which makes it possible to determine a major criterion of the grain quality, for example in view of determining the price and subsequent use of these grains.

Advantageously, the device furthermore makes it possible to ensure a homogenous spectral quality over a wider spectrum, which facilitates the pooling of the spectra for the later utilisation thereof during a fusion.

Advantageously, the device can be miniaturised and physically integrated in a system comprising several analysis modules with a reduced volume and a reduced weight.

Advantageously, the device is capable of processing a large volume of sample, which is particularly advantageous when the grains are very heterogenic, in order to reduce the impact of the sampling on the quality of the calibration and of the prediction.

Advantageously, the analysis time before calibration is reduced by two times, since one single analysis generates the two spectral outflows.

Advantageously, the cost of the device is reduced, which makes it possible to very significantly lower the sale price of it with respect to two, or even three separate devices, separately implementing an infrared spectroscopic measurement, a fluorescence spectroscopic measurement and a specific weight measurement.

In the following description, it will be understood that the specific weight of a sample is the weight per unit of volume of this sample, and measured in kilograms per hectolitre, for example of grains. It will be noted, that the definition of the specific weight is specific to the measurement on whole grains and meets the standards in force: the specific weight is not exactly equal to the density of a sample such as a fluid or a solid.

BRIEF DESCRIPTION OF THE DRAWINGS

Other characteristics and advantages of the present invention will emerge from the description made below, in reference to the appended drawings which illustrate embodiment examples of them, with no limiting character.

n the figures.

Naturally, to satisfy specific needs, a person skilled in the art can apply modifications in the following description. Although it refers to different embodiments, the present invention is not limited to these specific embodiments, and any modifications specific to the field of application of the present invention can be considered as clear for a person skilled in the art of the corresponding technique.

DETAILED DESCRIPTION OF AN EMBODIMENT

Figure 1A:
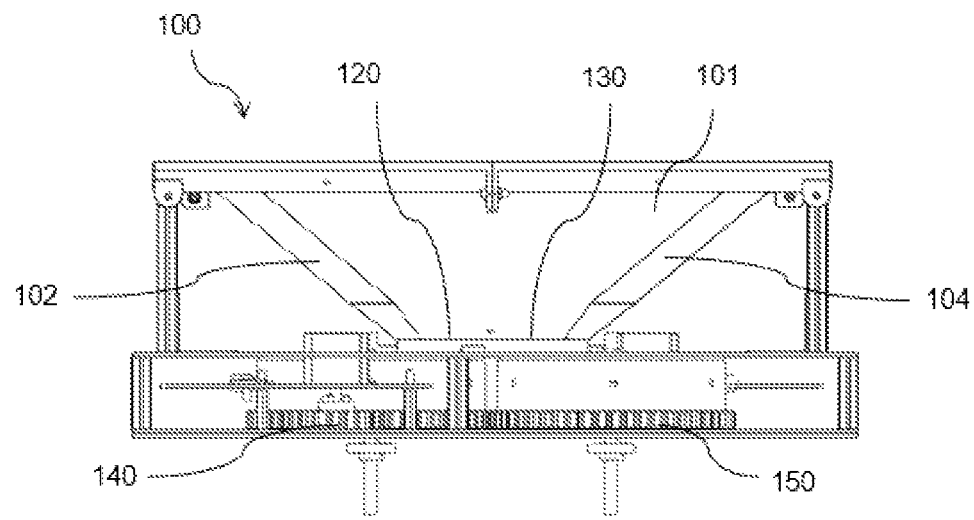
FIGS. 1a and 1b represent, respectively, a side view and a top view of a distribution funnel of a device according to an embodiment of the invention.
Figure 1B:
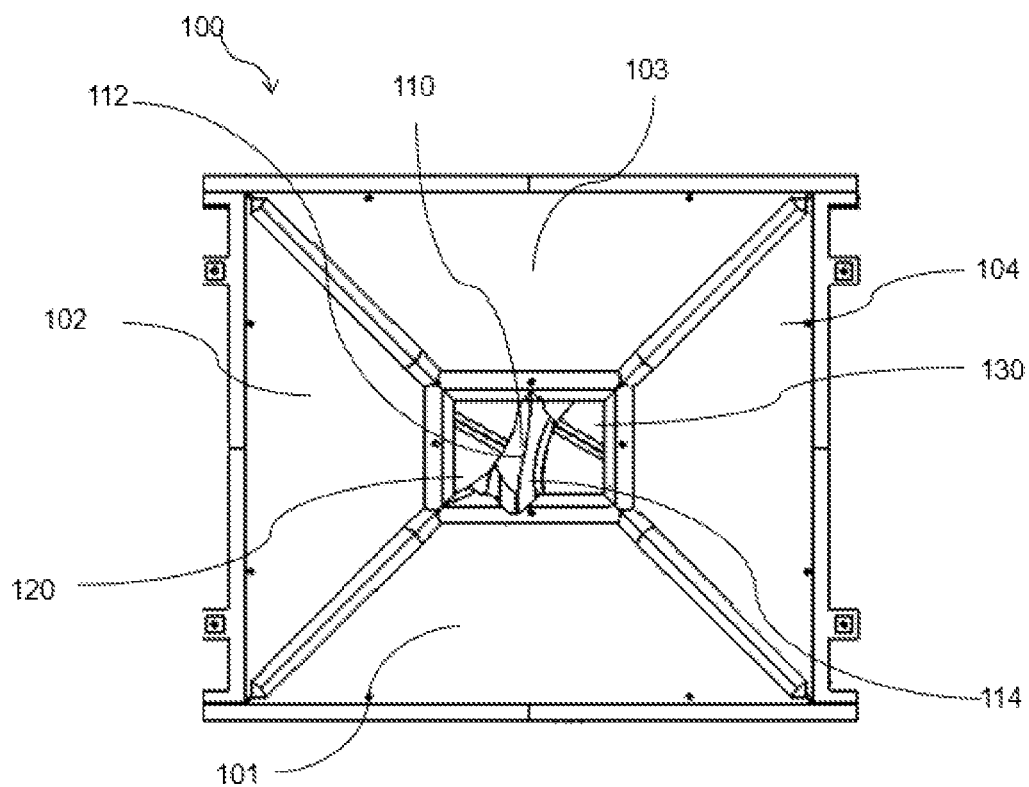

FIGS. 1a and 1b show a side view and a top view of a distribution funnel 100 of a device 1 according to the invention. A sample, for example a grain sample, is poured above the funnel 100 which subsequently guides it towards other elements of the device 1, as described below.

In a non-limiting manner, it will be considered below in the description that the sample poured into the funnel 100 is a grain sample. Generally, this sample can also comprise any grain, flour and/or semolina type, for example barley, wheat, malt, maize, rye, rapeseed, oat, triticale, soya, sunflower, buckwheat, spelt, peas, faba beans, lentils, vetches and/or hemp seed.

According to an embodiment of the invention, the funnel 100 has the shape of a funnel, for example a rectangular funnel comprising four faces 101, 102, 103 and 104. These four faces are inclined and adapted to guide the poured sample towards the lower portion of the funnel 100 under the effect of gravity. Each of the faces 101, 102, 103 and 104 is connected to at least one outflow from among a first outflow 120 and a second outflow 130, each of these two outflows being located in the lower portion of the funnel 100.

According to an embodiment of the invention, the two outflows 120 and 130 of the funnel 100 are separated from one another by at least one wall 110, for example a vertical wall comprising two faces 112 and 114. The two faces 112 and 114 are arranged so as to separate and to distribute the sample flowing into the funnel 100 in two volumes, a first volume being guided outside of the funnel 100 via the first outflow 120 and a second volume being guided outside of the funnel 100 via the second outflow 130. Generally, the first volume and the second volume are different.

The faces of the funnel 100 can be made of one single type of material or of different types of materials, comprising, for example metal, stainless steel or plastic, and are designed to make it possible for a fluid flow, continuous and without loss of the sample poured from the upper portion of the funnel towards one of the two outflows 120 and 130.

The two outflows 120 and 130 of the funnel 100 are connected to at least one analysis module by means of a conveyance guide, for example a pipe, a slider or a conveyor, which is configured to guide the sample towards this or these analysis module(s). To improve the guiding of the sample, split wheels 140 and 150 can be arranged between the outflows of the funnel and the conveyance guide to make the grains circulate from the funnel towards the conveyance guide.

According to an embodiment of the invention, the first outflow 120 and the second outflow 130 are distribution wheels. Preferably, the first outflow 120 is connected to a first analysis module 200, and the second outflow 130 is connected to a second analysis module 300. In a variant, the first outflow 120 and the second outflow 130 are furthermore connected to a third analysis module 400.

According to other non-represented embodiments of the present invention, the funnel 100 has the shape of a circular funnel. In a non-limiting manner, the funnel 100 comprises any number of faces, said faces could have various shapes, and which form a tapered, cylindrical or square funnel. The two outflows 110 and 120 as well as the wall 130 can be adapted to these different examples.

In reference to FIG. 1b, a grain sample poured above the funnel 100 is guided towards the first outflow 120 when it flows along the face 102 or along a portion of the face 103 and towards the second outflow 130 when it flows along the face 104, along a portion of the face 103 or along a portion of the face 101. According to another non-represented example, a grain sample poured above the funnel 100 is guided towards the first outflow 120 when it flows along the face 102 and along the face 103 of the funnel, and towards the second outflow 130 when it flows along the face 104 and along the face 101.

According to an embodiment of the invention, the wall 110 can be moved and/or oriented in view of modifying the manner of which the sample is separated into two volumes, and therefore to define specific values of the first volume guided outside of the funnel 100 via the first outflow 120 and of the second volume guided outside of the funnel 100 via the second outflow 130. For example, the wall 110 can be moved and/or oriented by a control device in order to modify the arrangement or the relative size of the first outflow 120 and of the second outflow 130.

Figure 2A:
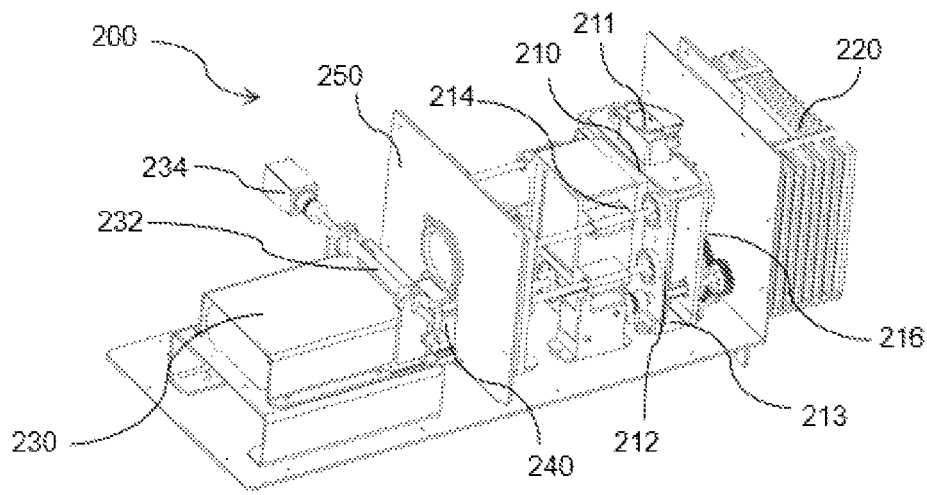
FIGS. 2a, 2b and 2c represent, respectively, a perspective view, a side view and a top view of a first analysis module of a device according to an embodiment of the invention.
Figure 2B:
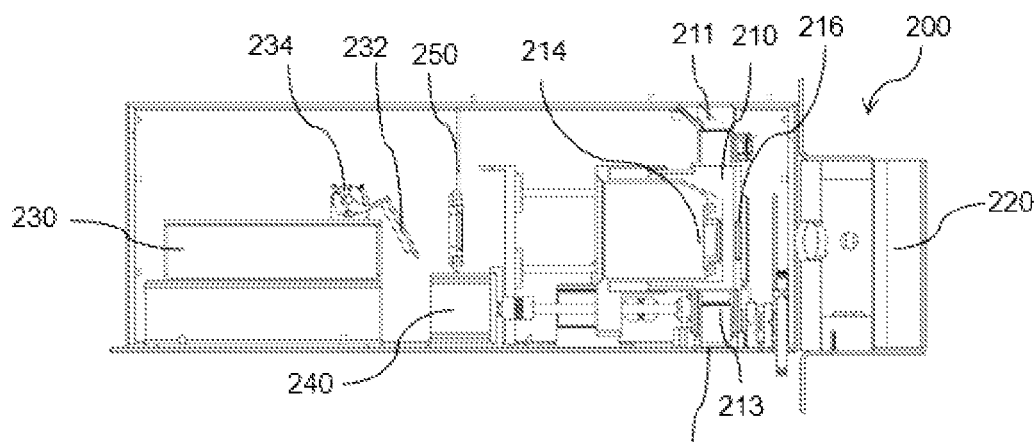
Figure 2C:
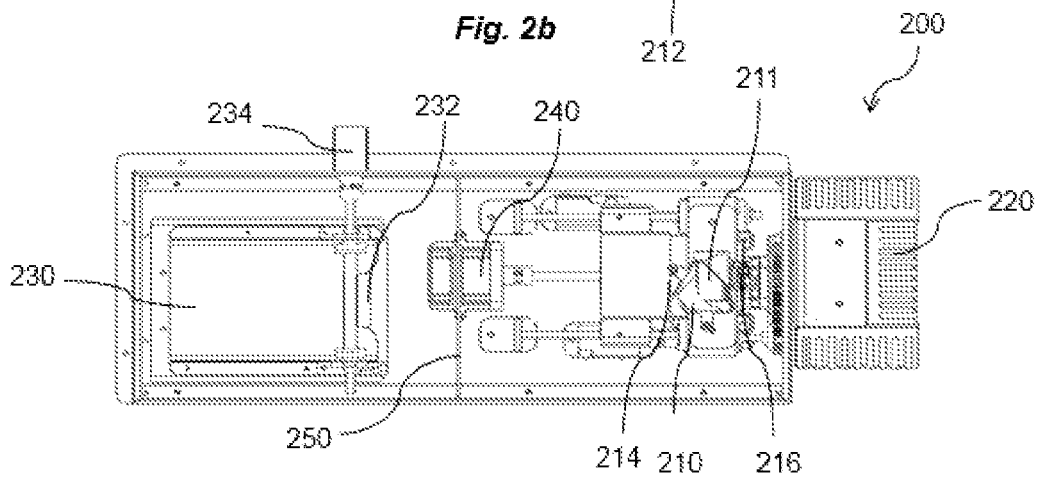

FIGS. 2a, 2b and 2c show a perspective view, a side view and a top view of a first analysis module 200 of a device 1 according to an embodiment of the present invention.

In particular, the first analysis module 200 is an infrared analysis module configured to acquire one or more spectra from a sample in the near infrared, for example one or more absorbance and/or transmittance spectra. Said infrared analysis module can also be configured to acquire one or more reflectance spectra.

In the framework of infrared spectroscopy principles, the infrared or near infrared spectrum of a sample is established by making an electromagnetic beam of wavelength comprised between 600 and 2500 nanometres pass through this sample. According to an embodiment of the invention, the electromagnetic beam is emitted by a continuous broad broadband source. In a variant, other types of sources can be used, for example one or more monochromatic sources.

The sample subjected to one or more infrared wavelength sources then emits an electromagnetic radiation spectrum. The analysis of these electromagnetic radiations and of the corresponding quantity of energy makes it possible to deduce thereof absorbance and/or transmittance spectra from the sample and, subsequently, to measure parameters such that the humidity rate, and protein rate, and sugar content, the hardness or also the particle size of a sample.

The first analysis module 200 comprises a first measurement chamber 210 configured to receive and contain a sample. According to an embodiment of the invention, the first chamber 210 comprises an inflow 211 to receive this sample, in particular the first volume of the sample guided outside of the funnel 100. Preferably, the inflow 211 comprises a funnel adapted to guide the sample towards the inside of the first chamber 210 and to fill it without loss, manually or automatically.

According to an embodiment of the invention, the first chamber 210 comprises detection elements, for example optical, mechanical or electronic detectors, configured to determine and indicate if a sample is present in the first chamber 210, and preferably which volume of this sample. These detection elements comprise, for example a detection sensor combining an infrared emitter and a photodiode to make it possible for a detection of the presence of a sample in the first chamber 210, and deduce from it if it is filled totally, partially, or not at all.

According to an embodiment of the invention, the first chamber 210 comprises, in a first end, a first wall 214 and in a second end, a second wall 216.

According to an embodiment of the invention, a portion of the wall 214 and of the wall 216 comprises a transparent window, for example a glass or plastic window. At least one of the two walls 214 and 216 is partially or completely transparent to electromagnetic radiations. Preferably, the window of the wall 216 is frosted so as to be partially or completely transparent to infrared electromagnetic radiations. Advantageously, the use of at least one window thus frosted improves the quality of the measurable spectra of the sample, and limits the dynamic range between these, and reference spectra measured in the absence of the sample.

In FIGS. 2a, 2b and 2c, the wall 216 is arranged on the side of a first excitation submodule 220 and the wall 214 is arranged on the side of the measurement submodule 230. Equally, the first excitation submodule 220 is an illumination submodule.

The first chamber 210 comprises a third outflow 212 to evacuate and guide the sample outside of it and outside of the first analysis module 200 towards another element of the device 1, or outside of the device 1. For example, the third outflow 212 can guide the sample towards an inflow of the second analysis module 300 or of the third analysis module 400. The third outflow 212, which can either be in the open position or in the closed position, is controlled manually or automatically.

According to an embodiment of the invention, a control of the third outflow 212 of the first analysis module 200 is carried out by means of a first draining system 213, this first draining system 213 comprising, for example a motor which can be controlled to open and close the third outflow 212 automatically.

According to an embodiment of the invention, the first wall 214 is a mobile wall and the second wall 216 is a fixed wall. In particular, the wall 214 is moveable along the main axis of the first analysis module 200 by means of a motor 240. The displacement of the wall 214 with respect to the wall 216 makes it possible to increase or to decrease the size of the first chamber 210, and thus to modify the thickness or the maximum volume of a sample which could be contained in the first chamber 210. The displacement of the wall 214 with respect to the wall 216, which can be automated, makes it possible to position it with a precision lower than 0.05 millimetres in a few seconds.

Due to the great diversity of the samples which can be analysed by the present device, for example through the size of the grains which compose this sample, the volume density of the sample contained in the first chamber 210 and the optical diffusion properties of this sample can highly vary from one case to another. For example, the spectral diffusion, absorption and amplification properties of wheat, maize and barley samples can be very different. Advantageously, an adjustment of the size of the first chamber 210 according to the present sample makes it possible to optimise the quality of the measurements taken by the first analysis module 200, when it is an infrared analysis module configured to acquire one or more absorption or transmission spectra of a sample in the infrared or in the near infrared.

The first analysis module 200 further comprises a first excitation submodule 220 and a second measurement submodule 230. According to an embodiment of the invention, and when the first infrared analysis module 200 is configured to acquire one or more transmittance spectra, each of these two submodules being arranged on either side of the first chamber 210. In a variant, these two submodules can be placed on one same side of the first chamber 210, for example to make it possible for the acquisition of reflectance spectra.

The first excitation submodule 220 is configured to emit an electromagnetic radiation, in particular an electromagnetic radiation of which the wavelength is in the infrared. This radiation is emitted by the first excitation submodule 220 in the direction of the first chamber 210 and of the second measurement submodule 230. The first submodule 220, the first chamber 210 and the second submodule 230 are aligned along an axis substantially defining the path of the radiations emitted by the first excitation submodule 220, then passing through the first chamber 210 and received by the second measurement submodule 230.

According to an embodiment of the invention, the first excitation submodule 220 comprises a continuous broadband light source, said light source being configured to emit an electromagnetic radiation, whose wavelength is comprised between 600 and 2500 nanometres.

For example, the excitation submodule 220 comprises a quartz-tungsten-halogen (QTH) lamp, which emits a light radiation from a heated tungsten filament. Preferably, said quartz-tungsten-halogen lamp is configured to be sub-supplied with a power comprised between 25 watts and 50 watts, and to emit a radiation in a range of wavelengths comprised between 240 and 2700 nanometres.

The first excitation submodule 220 is preferably arranged such that the radiations are emitted in the direction of the sample. These radiations are then absorbed by the sample or diffused by the sample and detected by the second measurement submodule 230, as detailed below. The second measurement submodule 230 is configured to transmit the measurements taken at any time towards a processing module.

Absorption spectroscopy is based on the principle according to which any material subjected to an incident radiation, for example an infrared radiation, can either reflect some of these radiations, or absorb some of these radiations, or transmit some of these radiations. In particular, absorbing radiations by the sample leads it to generate one or more absorption and/or transmission spectra.

The second measurement submodule 230 is arranged and configured to receive electromagnetic radiations emitted by the first excitation submodule 220 and electromagnetic radiations coming from the first chamber 210 and/or from a sample contained in this first chamber 210. According to an embodiment of the invention, the second measurement submodule 230 comprises a high sensitivity spectrometer which is configured to acquire one or more spectra, for example in the near infrared.

According to an embodiment of the invention, a spectrometer of the second measurement submodule 230 is integrated in a CMOS technology, for example on a silicon-on-insulator (SOI) wafer. According to another embodiment of the invention, the spectrometer of the second measurement submodule 230 comprises a CCD-type sensor, for example a BI-CCD detection strip with a slot of around 200 micrometres. Advantageously, such a spectrometer is sensitive to the infrared electromagnetic radiations emitted by a wide range of samples, in particular in the range of wavelengths comprised between 850 and 1100 nanometres.

The dynamic range of a spectrometer defines its detection range, corresponding to the ratio of the intensity of the largest signal and of the intensity of the smallest signal, measurable by this spectrometer. In particular, a spectrometer of the second measurement submodule 230 is characterised by a dynamic range equal to the maximum level divided by the minimum level of a signal measurable by this spectrometer, measuring a signal of minimum level corresponding to a measurement taken in the absence of a signal. Generally, a measurement taken in the absence of a signal can be implemented using one or more acquisitions of spectra in the absence of signal, for example 25 to 50 acquisitions, and by calculating the average, the effective value and/or the quadratic value of these acquisition to define the dynamic range of the spectrometer.

According to an embodiment of the invention, the elements of the first analysis module 200 are arranged in a fixed manner to avoid any movement of optical part except for the wall 214 if the latter is fixed. Furthermore, a spectrometer of the second measurement submodule 230 can be fixed thereto by one or more mechanical supports. Advantageously, such a configuration provides an optical chain which makes it possible for a stable and precise acquisition of transmittance spectra, in particular in the near infrared.

According to an embodiment of the invention, the first chamber 210 comprises diffusing elements 216. These diffusing elements 216 can be placed at the inflow of the first chamber 210 in the proximity of the wall 216 and of the first excitation submodule 220 and/or in the proximity of the wall 214 and of the second measurement submodule 230. When a sample is present in the first chamber 210, a large portion of the electromagnetic radiation emitted by the first excitation submodule 220 is absorbed by the latter and a lesser portion of this radiation is transmitted in the direction of the second measurement submodule 230. Generally, a sample illuminated by an infrared radiation absorbs a significant fraction of this radiation, which limits the intensity of the signal measured by a spectrometer.

Advantageously, the placement of diffusing elements, and in particular, infrared elements, at the inflow and/or at the outflow of the first chamber 210 makes it possible to improve the quality of the transmittance spectra measured by the second measurement submodule 230 in the infrared field and in the near infrared field. In particular, the placement of diffusing elements reduces the dynamic range to detect at least one order of magnitude without significantly modifying the time necessary to acquire spectra, of the order of 1% of the total measurement time.

According to an embodiment of the invention, the diffusing elements 216 comprise diffusion surfaces made of one or more materials chosen from among silicon, silica, sapphire or any type of material making it possible for an increased transmission of the electromagnetic radiations in the ranges of wavelengths of the infrared and of the near infrared. For example, the diffusing elements made of a silicon material preferably transmit the infrared radiations, but not the visible light radiations. Advantageously, the granularity of the diffusing elements 216 can be varied and selected in view of combining several of them to obtain the best compromise between reducing the dynamic range and limiting the loss of the signal measured.

To measure a signal and/or a spectrum of minimum level, the spectrometer of the second measurement submodule 230 comprises a shutter 232, for example a plate or an opaque element, which is connected to a rotating element 234, for example a motor, to move the shutter. The shutter 232 is moveable manually or automatically between a position distant from the inflow of the spectrometer and a position located in front of the inflow of this spectrometer. When the shutter 232 is in a distant position, the spectrometer is not hidden and receives all the electromagnetic radiations emitted towards it; when the shutter 232 is in front of the inflow of the spectrometer, the spectrometer is hidden and no electromagnetic radiation is measurable by it. This mechanism makes it possible for the spectrometer to acquire a spectrum coming from a sample contained in the first chamber 210 when the spectrometer is not hidden and a spectrum of minimum level, or noise, when the spectrometer is hidden.

According to an embodiment of the invention, the first analysis module 200 further comprises a plate 250 to separate and isolate the second measurement submodule 230 of the first chamber 210. The plate 250 comprises an opening which lets the electromagnetic radiations pass. According to another embodiment of the invention (not represented), no separation plate is present between the second measurement submodule 230 and the first chamber 210.

Figure 3A:
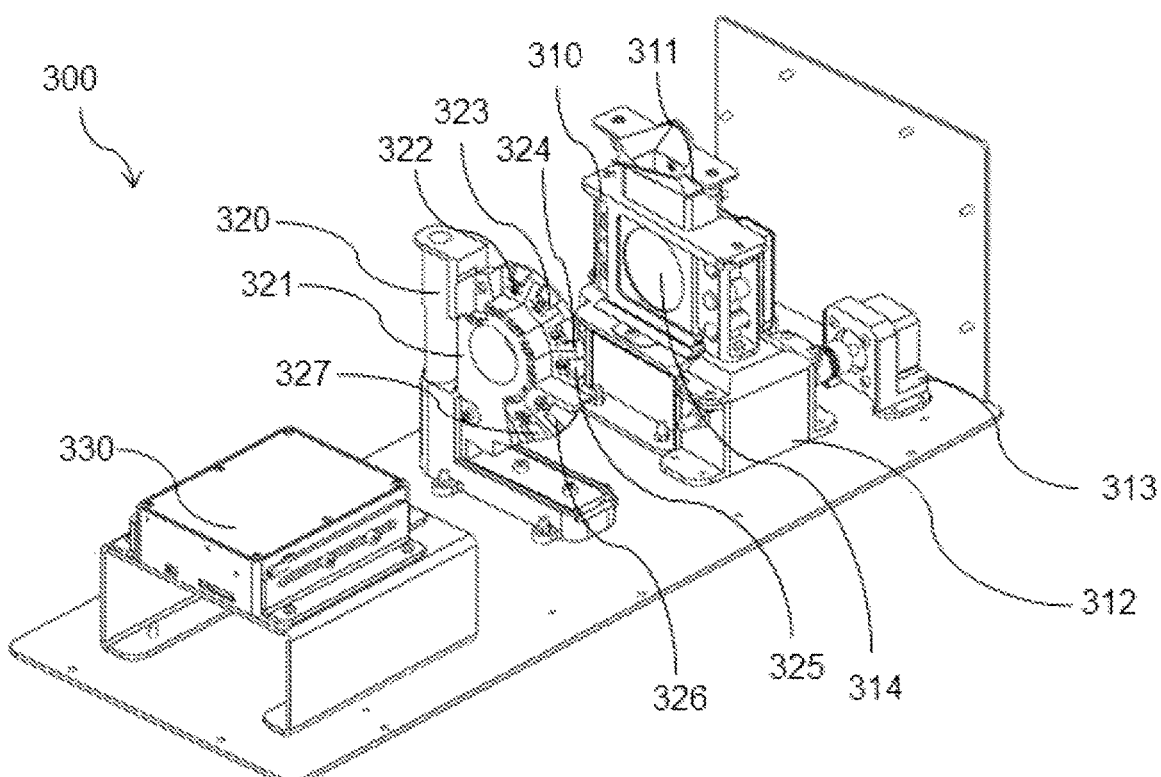
FIGS. 3a and 3b represent, respectively, a perspective view and a top view of a second analysis module of a device according to an embodiment of the invention.
Figure 3B:
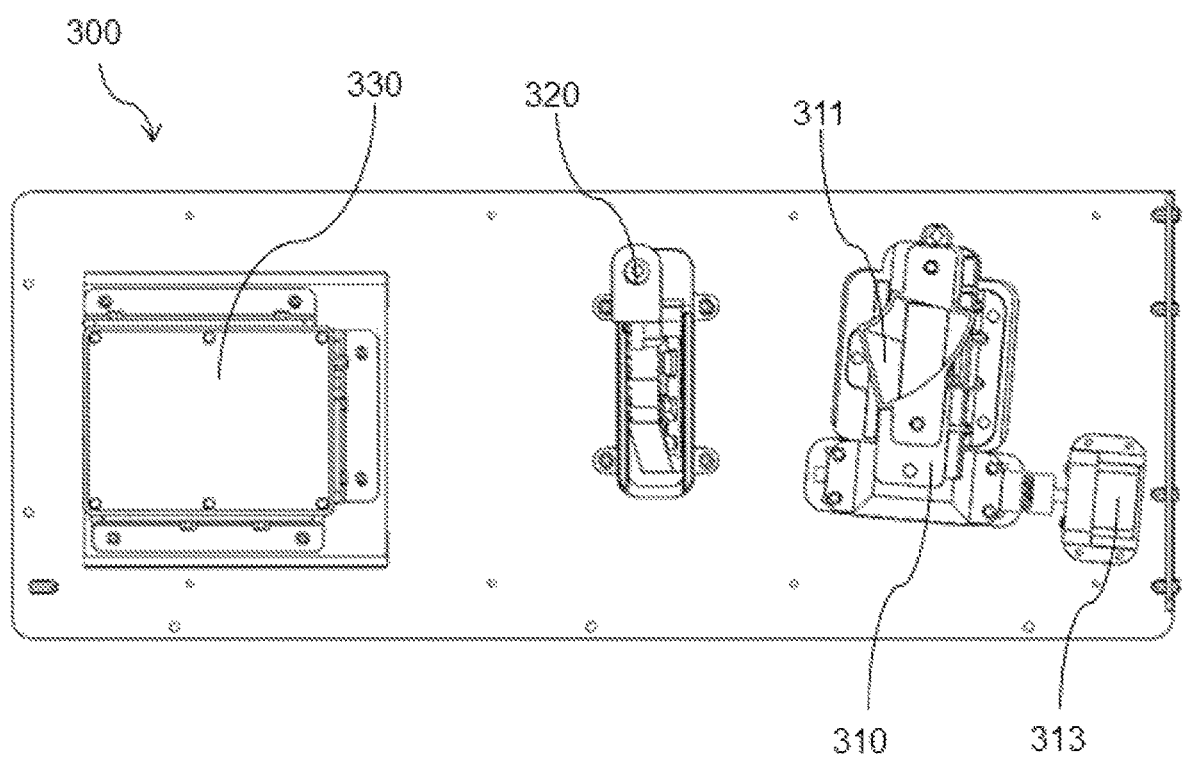

FIGS. 3a and 3b show a perspective view and a top view of a second analysis module 300 of a device 1 according to an embodiment of the present invention.

In particular, the second analysis module 300 is a fluorescence analysis module configured to acquire one or more fluorescence spectra of a sample, for example one or more frontal fluorescence spectra.

In the framework of fluorescence spectroscopy principles, a sample is excited by a light radiation of a determined wavelength, for example in the visible or ultraviolet field. The fluorescence spectra preferably extend over a spectral range comprised between 200 nanometres and 800 nanometres. The use of these wavelengths in the framework of conventional or frontal fluorescence spectroscopy methods makes it possible to measure parameters such as the Hagberg falling number or the mycotoxin, acrylamide contamination rate, etc. The Hagberg falling number, makes it possible to measure the alpha-amylase activity present in wheat grains, in particular, and/or to quickly detect contaminated or damaged samples, or also the varietal purity, at the entry thereof into the silo.

In response to this excitation, the sample emits a radiation, whose properties depend on the components contained in this sample. Based on the measurement of this emission radiation, it is then possible to deduce the corresponding fluorescence spectrum/spectra from this. The processing of these fluorescence spectra, preferably acquired over a spectral range comprised between 200 nanometres and 800 nanometres, using pre-processing, decomposition and modelling tools through development or other, makes it possible to extract information such as the Hagberg falling number, the mycotoxin contamination of other parameters characterising the degree of germination of the grains contained in a volume of the sample.

The second analysis module 300 comprises a second measurement chamber 310 configured to receive and contain a sample. According to an embodiment of the invention, the second chamber 310 comprises an inflow 311 to receive this sample, for example the second volume of the sample guided outside of the funnel 100. Preferably, the inflow 311 comprises a funnel adapted to guide the sample towards the inside of the first chamber 310 to fill it without loss, manually or automatically.

The second chamber 310 comprises a fourth outflow 312 to evacuate and guide the sample outside of the second analysis module 300 towards another element of the device 1, for example towards an inflow of a third analysis module 400. The fourth outflow 312, which can either be in the open position or in the closed position, is controlled manually or automatically. In particular, the opening and/or the closing of the fourth outflow 312 can be carried out manually or automatically by means of a second draining system 313, which can be motorised.

The second analysis module 300 is connected to the device 1. In particular, the fourth outflow 312 is connected to at least one analysis module, by means of a guide. Preferably, the fourth outflow 312 is connected to a third analysis module 400.

According to an embodiment of the invention, the second chamber 310 further comprises detection elements, for example optical, mechanical or electronic detectors, to determine if a sample is present in the second chamber 310 and preferably, which volume of this sample is present.

The second analysis module 300 further comprises a third excitation submodule 320 and a fourth measurement submodule 330, the configuration of each of these two submodules being preferably such that these are arranged on one same side of the second measurement chamber 310 to make it possible for a measurement of frontal fluorescence spectra.

In a variant, other configurations can be considered to make it possible to acquire conventional or frontal fluorescence spectra. For example, in the case of a configuration provided for the acquisition of frontal fluorescence spectra, the opening 314 of the second chamber 310 is arranged on the same side as the third excitation submodule 320 and as the fourth measurement submodule 330. In a variant, the third excitation submodule 320 and the fourth measurement submodule 330 can be placed on a different side of the second chamber 310 for the case of other configurations.

The third excitation submodule 320 is configured to generate and emit at least one electromagnetic radiation in the direction of the second chamber 310, in particular a visible or ultraviolet electromagnetic radiation of a wavelength comprised between 200 and 800 nanometres.

The third excitation submodule 320 is fixed stably in the second analysis module 300 and comprises an optomechanical part 321. This optomechanical part 321 comprises one or more light sources configured to emit electromagnetic radiations with predetermined illuminating wavelengths. Preferably, the or each of the light sources emits a monochromatic radiation with a given wavelength in the direction of the sample contained in the second chamber 320. According to the number of light sources, these electromagnetic radiations can roughly (several tens of wavelengths) or finely (several hundred of wavelengths) sample a spectral range, for example a spectral range covering the visible and ultraviolet fields.

In a non-limiting manner, the light sources of the optomechanical part 321 comprise a monochromatic radiation source or a polychromatic radiation source. For example, these light sources comprise a light-emitting diode or a laser source. The third excitation submodule 320 and/or the optomechanical part 321 can comprise other optical elements such as focalisation elements or diffusion elements, for example lenses. For example, the optomechanical part 321 comprises a lens configured to focalise or diffuse the electromagnetic radiations passing through it.

According to an embodiment of the invention, the optomechanical part 321 comprises an opening configured to let electromagnetic radiations pass, in particular the electromagnetic radiations emitted by the sample located in the second chamber 310, in the direction of the fourth measurement submodule 330.

According to an embodiment of the invention, the optomechanical part 321 is of a circular shape and comprises a given number of light sources, this number being comprised between one and twenty, and preferably comprised between one and ten.

In FIGS. 3a and 3b, the third excitation submodule 320 comprises six light-emitting diodes arranged along the circumference of the circular optomechanical part 321. The six light-emitting diodes 322 to 327, comprise four diodes 322, 323, 324 and 325 configured to emit an ultraviolet radiation of a central wavelength equal to 275+/−5 nanometres, a diode 326 configured to emit an ultraviolet radiation of a central wavelength equal to 338+/−3 nanometres, a diode 327 configured to emit an ultraviolet radiation of a central wavelength equal to 385+/−3 nanometres. Generally, each diode can be configured to supply a power comprised between 5 milliwatts and 1 watt. The third excitation submodule 320 can also comprise a seventh diode configured to emit an ultraviolet radiation of a central wavelength equal to 420+/−5 nanometres.

When it reaches the sample contained in the second chamber 320, an electromagnetic radiation emitted by one of the light sources of the optomechanical part 321 causes an excitation of the sample. When this sample is de-excited, it emits a complete fluorescence spectrum in all directions, and in particular, in the direction of the fourth measurement submodule 330.

According to an embodiment of the invention, the second chamber 310, the third excitation submodule 320 and the fourth measurement submodule 330 are aligned along an axis corresponding to the axis of the path of electromagnetic radiations emitted by the sample in the second chamber 320 in the direction of the fourth measurement submodule 330. The fourth measurement submodule 330 is placed so as to be able to receive the electromagnetic radiations coming from the sample contained in the second chamber 310 after the excitation of this sample. The fourth measurement submodule 330 is configured to transmit the measurements taken at any time towards a processing module.

According to an embodiment of the invention, the fourth measurement submodule 330 comprises a spectrometer configured to measure one or more fluorescence spectra, for example a frontal fluorescence spectrum in the ultraviolet and the visible, and corresponding to wavelengths comprised between 200 and 800 nanometres. The spectrometer of the fourth measurement submodule 330 is arranged substantially on the same side as the third excitation submodule 320 to make it possible to acquire frontal fluorescence spectra. Comparatively to the other types of fluorescence spectra, the acquisition of frontal fluorescence spectra makes it possible to avoid generating too many large analytical errors connected to the sample, to its preparation or to the external conditions like temperature or pressure; the results obtained are therefore precise and determined more quickly.

Just like for the spectrometer of the second measurement submodule 230, the spectrometer of the fourth measurement submodule 330 is configured to furthermore acquire a signal and/or a minimum level spectrum. This acquisition can be implemented without requiring any shutter, by taking a measurement when the light source(s) of the third excitation submodule 320 are off.

According to an embodiment of the invention, the spectrometer of the fourth measurement submodule 330 comprises a CCD-type sensor with a slot of around 500 micrometres and a resolution of around 10 nanometres.

According to other embodiments not represented, the third excitation submodule 320 can be arranged in different positions and orientations in the second analysis module 300. For example, the third excitation submodule 320 can be arranged along an axis substantially perpendicular to another axis passing through the second chamber 310 and by the second measurement submodule 330, in order to acquire right-angled fluorescence spectra.

According to an embodiment of the invention, the second chamber 310, the third excitation submodule 320 and the fourth measurement submodule 330 are fixed in the second analysis module 330 by one or more mechanical supports. This configuration avoids any movement of mechanical part, and provides an optical chain making it possible for a stable and precise acquisition of fluorescence spectra, in particular frontal fluorescence spectra and/or other types of spectra. Advantageously, the second analysis module 300 is compact and does not integrate any mobile optical parts. This compactness and this stability improve the sensitivity and the repeatability of the measurements during the acquisition of fluorescence spectra while facilitating the instrumental standardisation.

According to an embodiment of the invention, the filling of the second chamber 310, the excitation of the sample by the excitation submodule 320 and the acquisition of fluorescence spectra by the second measurement submodule 330 are automated mechanically and electronically.

According to an embodiment of the invention, a control of the fourth outflow 312 of the second analysis module 300 is carried out by means of a second draining system 313, this second draining system 313 comprising, for example a motor which can be controlled to open and close the fourth outflow 312.

Figure 4A:
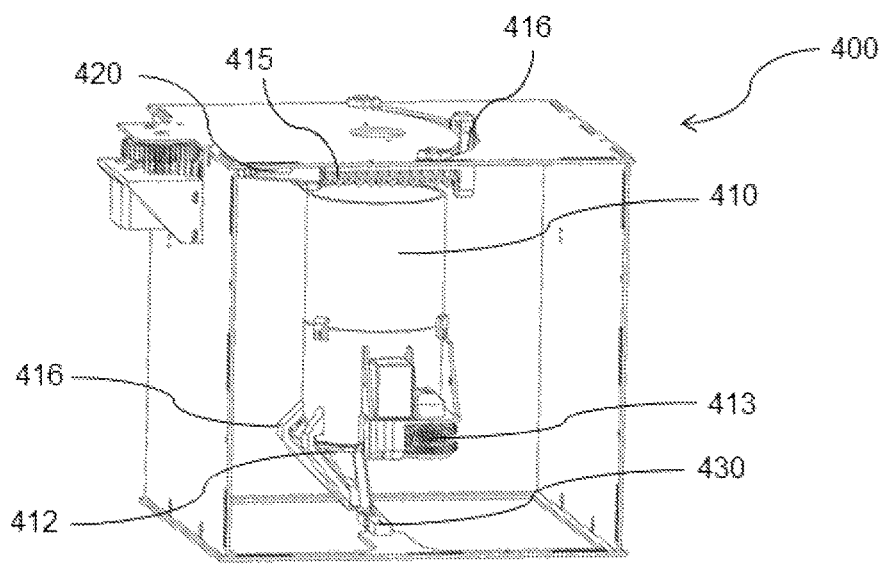
FIGS. 4a, 4b and 4c represent, respectively, a perspective view, a side view and a top view of a third analysis module of a device according to an embodiment of the invention.
Figure 4B:
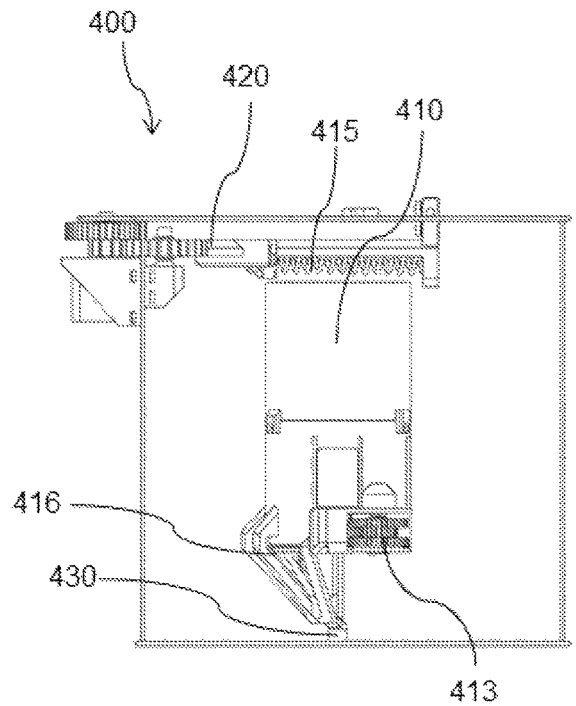
Figure 4C:
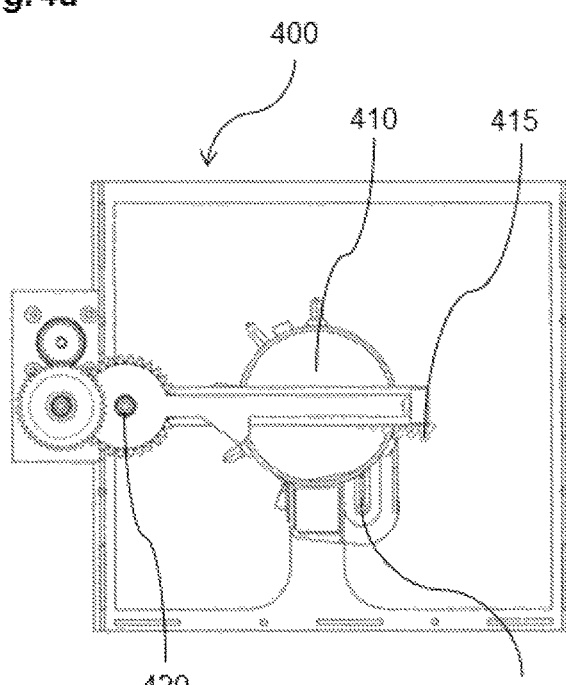

FIGS. 4a, 4b and 4c show a perspective view, a side view and a top view of a third analysis module 400 of a device 1 according to an embodiment of the present invention. According to an embodiment of the invention, the third analysis module 400 is a module for measuring weight configured to measure the specific weight of a sample.

The third analysis module 400 and connected to the rest of the device 1. According to an embodiment of the invention, the third analysis module 400 is connected to the third outflow 212 of the first chamber 210 and to the fourth outflow 312 of the second chamber 310 in order to measure the specific weight of the same sample as that coming from the first analysis module 200 and of the second analysis module 300. In a variant, the third analysis module 400 is connected to the first outflow 120 and/or to the second outflow 130 of the funnel 100.

The third analysis module 400 comprises a container 410 configured to receive and contain a portion of the sample. The base of the container 410 is supported by a platform 416 which stabilises it and which can have different dimensions and geometries.

According to an embodiment of the invention, the container 410 is a container which has a cylindrical, parallelepiped, or also tapered shape. This container comprises a filling volume comprised between 100 millilitres and 1000 millilitres, preferably 500 millilitres.

According to an embodiment of the invention, the third analysis module 400 comprises a fifth measurement submodule 430 arranged under the container 410. The fifth measurement submodule 430 comprises one or more weight sensors configured to measure the weight of the container 410 when this is empty or filled with a sample, partially or completely.

According to an embodiment of the invention, the third analysis module 400 comprises detection elements, for example optical or mechanical detectors, to determine if a sample is present in the container 410, and preferably, what volume of this sample.

According to an embodiment of the invention, the third measurement module 400 comprises a levelling element 415, for example a levelling strip or a levelling spring, configured to be moved above the container 410, or in this container 410, in order to retrofit a sample contained in the container 410.

The displacement of the levelling element 415 is automated, and guarantees a measurement of the weight of the sample contained in the container 410 which has an excellent repeatability.

According to an embodiment of the invention (not represented), the levelling element 415 comprises a cleaning element and/or resetting element.

The fifth measurement submodule 430 is configured to transmit the measurements taken at any time towards a processing module, to calculate the specific weight of any sample contained in the container 410 from the weight measured and of the volume measured of this sample. Advantageously, the third analysis module 400 provides a compact and precise means to measure, with high precision, the specific weight of a grain sample, such that it can be reproduced on a site outside or inside a grain silo.

The container 410 comprises a fifth outflow 412 to evacuate and guide the sample outside of it and outside of the third analysis module 400, for example towards the outside of the device 1. The fifth outflow 412, which can either be in the open position or in the closed position, can be controlled manually or automatically. According to an embodiment of the invention, a control of the fifth outflow 412 of the third analysis module 400 is carried out by means of a third draining system 413, this third draining system 413 comprising, for example a motor which can be controlled to open and close the fifth outflow 412.

According to an embodiment of the invention (not represented), the third analysis module 400 comprises a cleaning system, which is configured to clean the platform 416 and/or inside the container 410 before or after an evacuation of the sample outside of the container 410.

The third analysis module 400 thus makes it possible for a precise measurement of the specific weight of a sample contained in the container 410 can be obtained from the measurement of the weight of the sample in the container. The third analysis module 400 makes it possible, furthermore, for a measurement of the tare weight, i.e. of the weight of the container when it is empty. By subtracting the tare weight measured of the weight obtained in the presence of the sample and by using a calibration equation, it is thus possible to precisely determine the specific weight of the sample.

Figure 5:
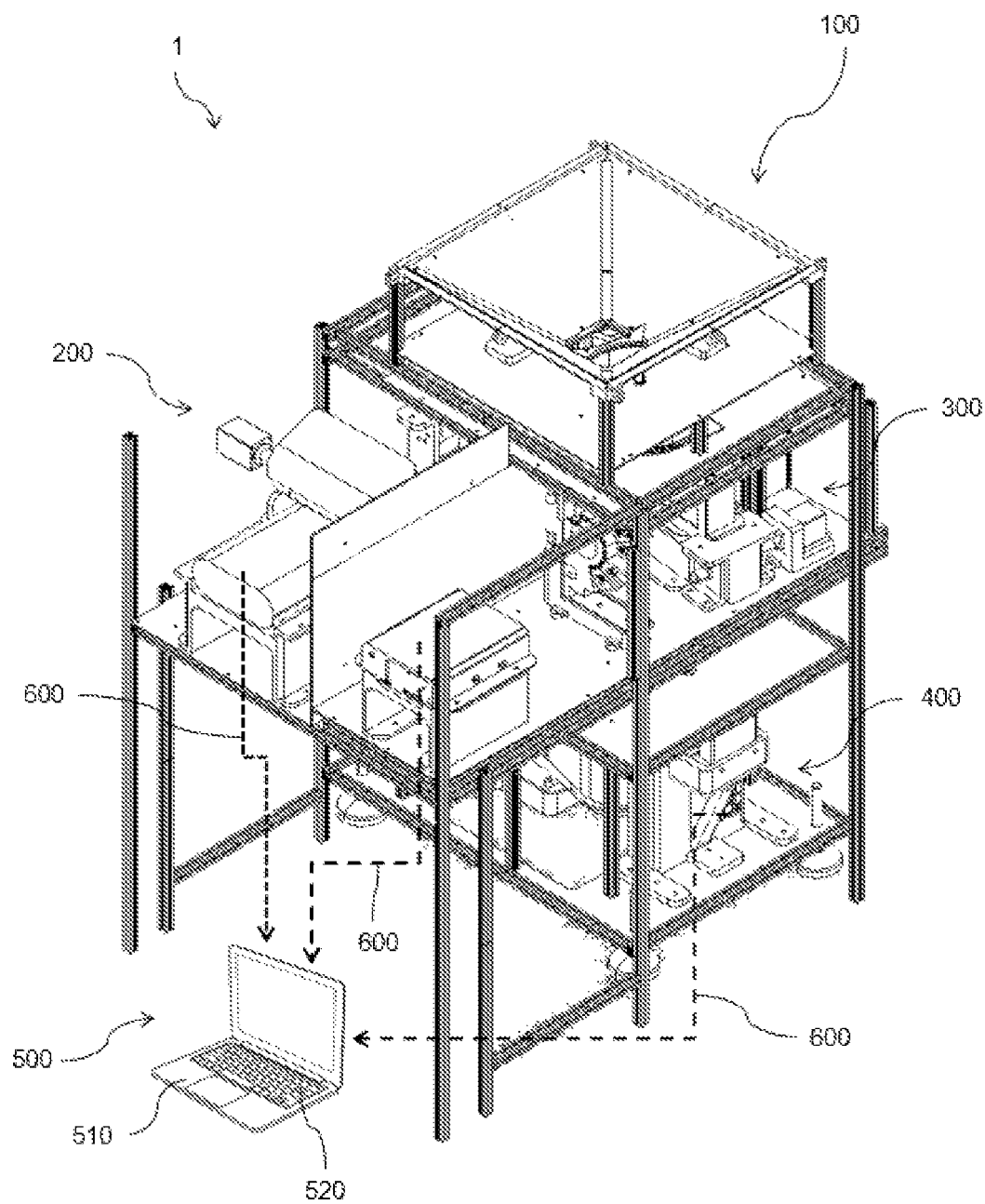
FIG. 5 represents a perspective view of a device according to an embodiment of the invention.
Figure 6:
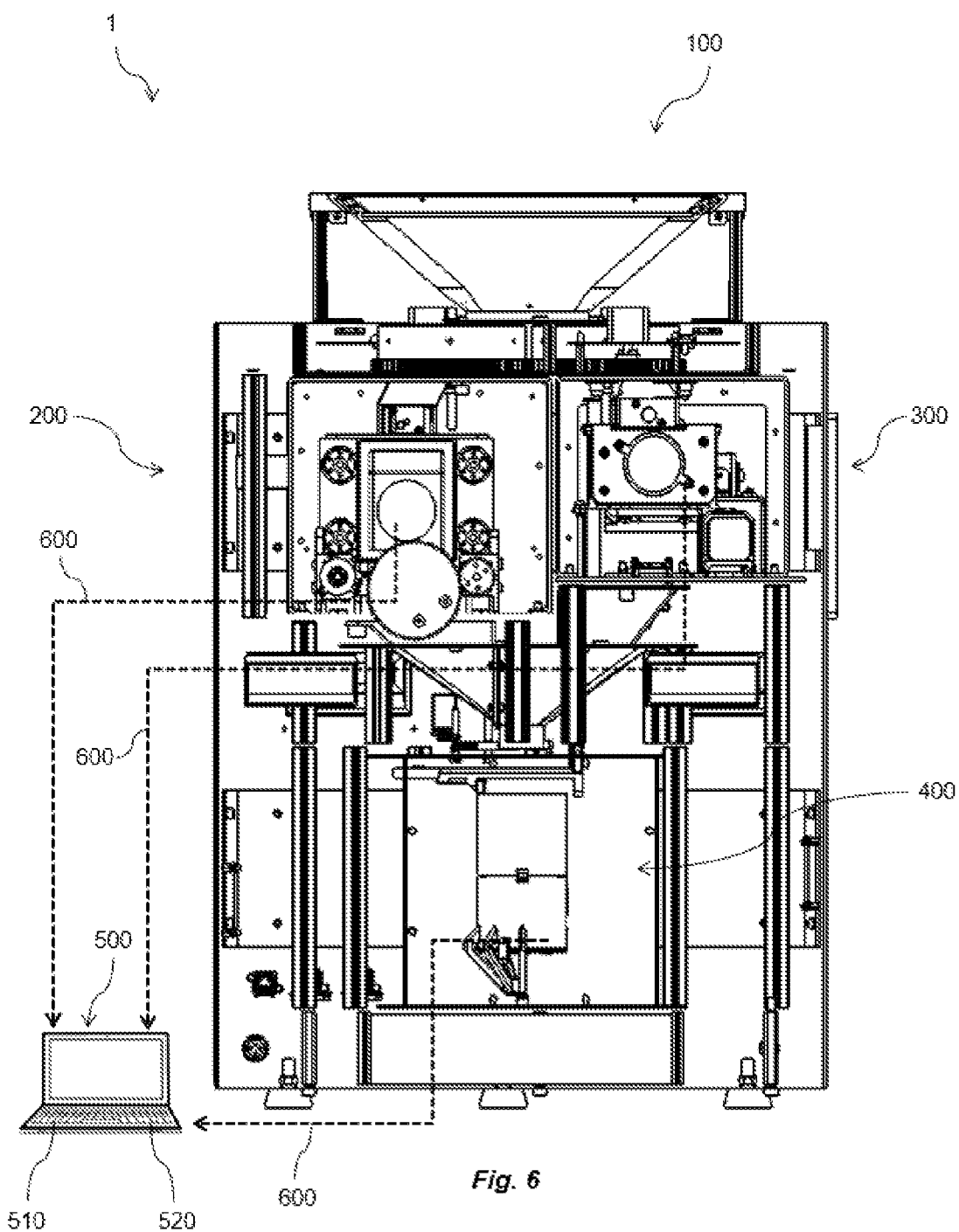
FIG. 6 represents a side view of a device according to an embodiment of the invention.

FIGS. 5 and 6 show, respectively, a perspective view and a side view of a device 1 according to the invention, the device 1 comprising the funnel 100, the first analysis module 200, the second analysis module 300 and the third analysis module 400 described above.

According to an embodiment of the invention, the distribution funnel 100 and the third analysis module 400 are each connected to the first analysis module 200 and to the second analysis module 300 by means of guides in order to make it possible to guide a sample from the distribution funnel 100 towards the first analysis module 200 and towards the second analysis module 300, then each of the first and second analysis modules 200 and 300 towards the third analysis module 400, under the effect of gravity. The sample is then evacuated below the third analysis module 400.

The device 1 further comprises a processing module 500. In FIGS. 5 and 6, the processing module 500 is represented as a laptop, but which can also be any type of electronic or computerised processing means, for example a processor, a desktop computer, a smartphone or any device similar to a terminal with a control screen, a USB stick, a mobile memory card or any other similar technology. Preferably, the processing module 500 is an embedded PC.

The processing module 500 is connected to the device 1, in particular to one or more analysis modules of the device 1, by means of a communication network 600. The communication network 600 makes it possible to connect the processing module 500 to the analysis modules 200, 300 and 400. For example, the communication network 600 is a local network, such as a wired network, a Bluetooth network, a wi-fi network or also an Ethernet network. In any case, the communication network 600 is configured to transmit information between the processing module 500 and each analysis module of the device 1.

According to an embodiment of the invention, the processing module 500 is configured to control the circulation of the sample in the different elements of the device 1, for example via the inflow and outflow control of the analysis modules 200, 300 and 400 and/or the funnel 100. Advantageously, the processing module 500 makes it possible to manage, either manually or automatically, the measurements taken by the device 1 by following method steps such as described below with respect to FIG. 7.

The processing module 500 comprises a memory 510 which is configured to receive data transmitted by the communication network 600. This data can comprise any type of information measured by the analysis modules such as wavelengths of radiations emitted by the sample in any one of the analysis modules, the intensities measured of these radiations, corresponding electromagnetic spectra or also tare weights and specific weights measured by the third analysis module 400.

In FIGS. 5 and 6, the discontinuous arrows represent the direction of data transmissions by the communication network 600, of a first element towards a second element. For example, the communication network 600, the transmission of an infrared spectrum acquired by the first analysis module 200 towards the processing module 500, of a fluorescence spectrum acquired by the second analysis module 300 towards the processing module 500 or also a specific weight measured by the third analysis module 400 towards the processing module 500.

The processing module 500 further comprises a processor 520 which is configured to carry out operations on data contained in the memory 510. Different software installed on the processor 520 can be used to carry out these operations. In particular, the processor 520 is configured to carry out a coupling of spectra, for example a coupling of an infrared spectrum coming from the first analysis module 200 and a fluorescence spectrum coming from the second analysis module 300, to produce a mixed spectrum. Furthermore, the processor 520 of the processing module 500 is configured to determine at least one indicator of the quality of the sample from this data or these spectra.

The processor 520 is configured to organise the data and the spectra in order to carry out a digital and computerised processing of it, in particular, the fluorescence spectra, the infrared spectra and the specific weights acquired by the analysis modules 200, 300 and 400. For example, the processor 520 organises the fluorescence data into three-dimensional mathematical tables, these three dimensions corresponding respectively to the wavelength of the excitation electromagnetic radiations used, to the wavelength of the emission radiation of the sample measured in response to this excitation by a spectrometer, and to the intensity of this emission radiation. The processor 520 organises the infrared data into separate mathematical tables, for example two- or three-dimensional.

The processor 520 is configured to carry out a coupling of data and spectra, and more specifically, data organised in the mathematical tables. For example, a first technique consists of concatenating the mathematical tables of the fluorescence data and infrared data in one same mathematical table. Advantageously, this first technique returns to juxtapose the spectra corresponding to this data over the whole range of wavelengths of the spectra acquired. A second technique consists of constructing a spectral image of the sample from the combination of fluorescence spectra and of infrared spectra. Advantageously, this combination makes it possible to obtain a three-dimensional image which conserves the three-dimensional structure of the mathematical table of the associated fluorescence data. A third technique consists of constructing a two-dimensional spectral image resulting from the combination of the first technique and of the second technique.

To carry out the couplings of spectroscopic data and determine the quality indicators such as a Hagberg falling number, a mycotoxin contamination rate, an acrylamide contamination rate, a humidity rate, a protein rate, a sugar content, a hardness, a baking strength or other characteristic typical of flours, a particle size or also a specific weight, the reference work by D. Bertrand and E. Dufour, "La spectroscopie infrarouge et ses applications analytiques" ("Infrared spectroscopy and the analytical applications thereof") (2006) can be referred to, for the case of data coming from infrared spectra and the journal by J. Sadecka and J. Tothova, "Fluorescence Spectroscopy and Chemometrics in the Food Classification—A Review", Czech Journal of Food Sciences 25(4):159-173 (2007) can be referred to, for the case of data coming from fluorescence spectra. For data fusion, different methods alluded to in the journal, "Data fusion methodologies for food and beverage authentication and quality assessment—A review", Analytica Chimica Acta 2015, 891, 1-14 can be referred to.

A breakdown of data before or after fusion is then implemented by applying multivariate or multipath statistical models known from the technical field, in view of predicting one or more quality indicators. The measurements of specific weights coming from the third analysis module 400 make it possible for a user or for the processing module 500 to select, with more precision, the statistical models corresponding to the type of sample analysed.

Moreover, the processor 520 is configured to determine at least one indicator of quality of the sample from the data and the spectra coupled by one or other of these techniques. According to an embodiment of the invention, these quality indicators are selected from among: a Hagberg falling number, a mycotoxin contamination rate, an acrylamide contamination rate, a protein rate, a sugar content, a baking strength or other characteristic of flours, a hardness, a particle size or also a specific weight.

Advantageously, calculating indicators of quality of a sample from coupled data rather than data obtained separately makes it possible to improve the precision of the prediction of quality indicators selected from among the humidity rate, the protein rate, the mycotoxin contamination rate, the Hagberg falling number or also the specific weight. The knowledge of the specific weight of the sample measured in the third analysis module 400 makes it possible to further improve the precision of this prediction, via a selection of the statistical models adapted to the sample analysed by the device 1.

According to an embodiment of the invention, the maximum dimensions of the device 1 are 75 centimetres high, 70 centimetres wide and 55 centimetres deep. For example, the dimensions of the device 1 are of around 71 centimetres high, 65 centimetres wide and 45 centimetres deep. Preferably, the dimensions of the device 1 are of around 60 centimetres high, 55 centimetres wide and 50 centimetres deep.

According to an embodiment of the invention, the device 1 and/or some of the elements thereof are contained in a sealed casing in order to isolate them from the external conditions, like for example the presence of dust, the fluctuation of the temperature or also impacts connected to the transportation of the device.

Figure 7:
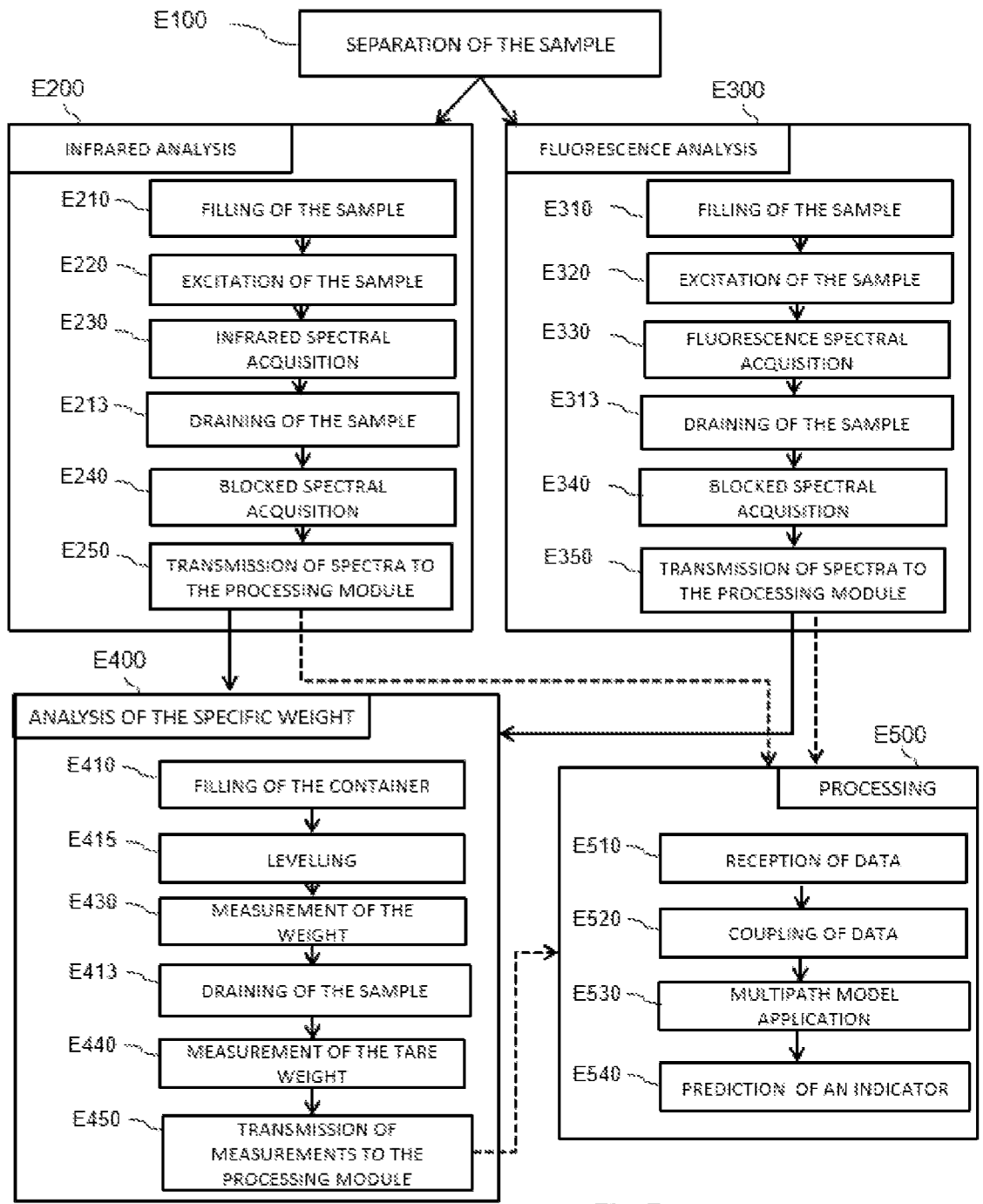
FIG. 7 represents, in flowchart form, steps of an analysis method according to an embodiment of the invention.

FIG. 7 shows, in the form of a flowchart, steps of a method for analysing a sample according to an embodiment of the invention. According to an embodiment of the invention, the method comprises a first separation step E100 during which a sample poured into the funnel 100 of the device 1 is separated and guided towards a first analysis module 200 and towards a second analysis module 300. A second analysis step E200 and a third analysis step E300 are then carried out, either successively or simultaneously.

According to an embodiment of the invention, the second analysis step E200 implemented by the first analysis module 200 aims to acquire an infrared or near infrared spectrum of the sample and comprises the following steps: a sub-step E210 of filling the first chamber 210 by a sample, a sub-step E210*b* of detecting the filling of the first chamber 210 by the detection elements of the first analysis module 200, a sub-step E220 of exciting the sample by the first excitation submodule 220, a sub-step E230 of acquiring by the first acquisition module 230, at least one infrared or near infrared spectrum by the first measurement module 230, a sub-step E213 of evacuating the sample outside of the first chamber 210 and towards the third analysis module 400 via the first draining system 213, a sub-step E240 of acquiring at least one spectrum blocked by the first module 230 when the spectrometer of the first module 230 is blocked by the shutter 232 and a sub-step E250 of transmitting the spectra acquired during the step E200 towards the processing module 500.

According to an embodiment of the invention, a step of taking the reference spectrum, i.e. a spectrum step of the empty source precedes the filling sub-step E210. In a variant, this step of taking the reference spectrum can directly follow the sub-step E213 of evacuating the sample.

In a variant, the sub-step E213 of evacuating the sample can be implemented after one or the other, from among the sub-step E240 of acquiring at least one blocked spectrum and the transmission sub-step E250. According to another variant, the sub-step E240 of acquiring at least one blocked spectrum can be implemented before the sub-step E210 of filling the first chamber 210 by a sample. The filling sub-step E210 can further comprise a sub-step E210b of detecting the filling of the first chamber 210 by detection elements of the first analysis module 200.

According to an embodiment of the invention, the third analysis step E300 implemented by the second analysis module 300 aims to acquire at least one fluorescence spectrum of the sample and a blocked spectrum via the following sub-steps: a sub-step E310 of filling the second chamber 310 by a sample, a sub-step E320 of exciting the sample by the third excitation submodule 320, an acquisition sub-step E330 by the fourth measurement submodule 330 of at least one fluorescence spectrum, a sub-step E313 of evacuating the sample outside of the second chamber 310 via the second draining system 313, a sub-step E340 of acquiring at least one blocked spectrum by the fourth measurement submodule 330 when the light sources of the third excitation submodule 320 are switched off and a sub-step E350 of transmitting spectra acquired during the third step E300 towards the processing module 500. In a variant, the sub-step E313 of evacuating the sample can be implemented after one or the other, from among the sub-step E340 of acquiring at least one blocked spectrum and the transmission sub-step E350. The filling sub-step E310 can further comprise a sub-step E310b of detecting the filling of the second chamber 310 by detection elements of the second analysis module 300.

According to an embodiment of the invention, the fourth analysis step E400 implemented by the third analysis module 400 aims to measure at least one specific weight of the sample and a tare weight via the following sub-steps: a sub-step E405 of measuring the tare weight corresponding to the empty weight of the container 410, a sub-step E410 of filling the container by a sample, a sub-step E415 of levelling the surface of the sample by the levelling element 415, a sub-step E420 of measuring the specific weight of the sample contained in the container, a sub-step E440 of evacuating the sample outside of the container 410 by the third draining system 413, and a sub-step E450 of transmitting measurements taken of the specific weight and of the tare weight to the processing module 500. The filling sub-step E410 can further comprise a sub-step E410b of detecting the filling of the container 410 by a sample, by means of the detection elements of the third analysis module 400.

According to an embodiment of the invention, the fifth processing step E500 implemented by the processing module 500 aims to determine an indicator of quality of the sample via the following sub-steps: a sub-step E510 of receiving data coming from the first analysis module 200, of the second analysis module 300 and of the third analysis module 400, a sub-step E520 of coupling this data, a sub-step E530 of applying at least one multipath statistical model and a sub-step E540 of predicting at least one quality indicator based on the preceding sub-steps. The fifth processing step E500 can furthermore include a sub-step E525 not represented in FIG. 7 consisting of determining at least one multipath statistical model according to the value of the specific weight of the sample transmitted to the processing module 500 during the sub-step E450, said sub-step E525 being implemented before the sub-step E530 of applying at least one multipath statistical model.

Naturally, to satisfy specific needs, a person skilled in the field of the invention can apply modifications in the preceding description. Although the present invention has been described above in reference to specific embodiments, the present invention is not limited to the specific embodiments, and the modifications which are found in the field of application of the present invention will be obvious for a person skilled in the art.

The invention claimed is:

1. A device for spectroscopically analysing a grain sample, wherein said device comprises a first infrared analysis module, a second fluorescence analysis module, a third specific weight analysis module and a processing module, each of said first analysis module and said second analysis module comprising
    a measurement chamber configured to receive at least a portion of the sample;
    an excitation submodule configured to emit at least one electromagnetic radiation towards said at least a portion of the sample;
    a measurement submodule configured to acquire at least one electromagnetic spectrum of the sample;
    a draining system configured to guide the sample towards said third analysis module;
    the third analysis module comprising
    a container configured to receive the sample;
    a measurement submodule configured to measure a specific weight of the sample;
    said processing module being connected to each of the analysis modules by a communication network and comprising
    a memory configured to receive data transmitted by said communication network, said data comprising electromagnetic spectra acquired by said first analysis module and said second analysis module and specific weights measured by said third analysis module; and
    a processor configured to organise and couple the data received in the memory and to determine an indicator of quality of the sample from the coupled data.

2. The device according to claim 1, wherein the excitation submodule of the first analysis module is configured to emit at least one electromagnetic radiation of wavelength comprised between 600 and 2500 nanometers, and wherein the measurement submodule of the first analysis module comprises a spectrometer configured to acquire at least one absorbance and/or transmittance spectrum.

3. The device according to claim 1, wherein the excitation submodule of the second analysis module is configured to emit at least one electromagnetic radiation of wavelength comprised between 200 and 800 nanometers and the measurement submodule of the second analysis module comprises a spectrometer configured to acquire at least one spectrum selected from among: a fluorescence spectrum in frontal mode, acquired at an angle comprised between 30 and 60° with respect to the surface of the sample, and a conventional fluorescence spectrum, acquired at a right angle, a wavelength of said at least one spectrum being comprised between 200 nanometers and 800 nanometers.

4. The device according to claim 1, wherein said device further comprises a funnel configured to guide at least a portion of the sample towards the first analysis module and the second analysis module.

5. The device according to claim 1, wherein said indicator of quality of the sample is selected from among: a Hagberg falling number, a mycotoxin contamination rate, an acrylamide contamination rate, a humidity rate, a protein rate, a sugar content, a hardness, a particle size or also a specific weight.

6. The device according to claim 1, wherein the height of the device is less than 75 centimeters, the width of the device is less than 70 centimeters, and the depth of the device is less than 55 centimeters.

7. The device according to claim 6, wherein the height of the device is less than 60 centimeters, the width of the device is less than 55 centimeters, and the depth of the device is less than 50 centimeters.

\* \* \* \* \*